(12) United States Patent
Deininger et al.

(10) Patent No.: US 8,209,016 B2
(45) Date of Patent: Jun. 26, 2012

(54) IMPLANTABLE LEAD MANAGEMENT

(75) Inventors: Steve T. Deininger, Blaine, MN (US); John E. Kast, Hugo, MN (US); Raymond F. McMullen, Shorewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 206 days.

(21) Appl. No.: 12/725,548

(22) Filed: Mar. 17, 2010

(65) Prior Publication Data

US 2010/0241205 A1    Sep. 23, 2010

Related U.S. Application Data

(60) Provisional application No. 61/161,906, filed on Mar. 20, 2009.

(51) Int. Cl.
*A61N 1/375* (2006.01)
(52) U.S. Cl. ........................................................ 607/36
(58) Field of Classification Search ...................... 607/36
See application file for complete search history.

(56) References Cited

U.S. PATENT DOCUMENTS

| 5,217,493 | A | 6/1993 | Raad |
| 5,218,959 | A * | 6/1993 | Fenster ............................ 607/36 |
| 5,624,704 | A | 4/1997 | Darouiche |
| 6,216,042 | B1 | 4/2001 | Robertson |
| 6,327,507 | B1 | 12/2001 | Buchan |
| 7,831,313 | B2 * | 11/2010 | Lauro ............................ 607/126 |
| 2005/0015128 | A1 | 1/2005 | Rezai |
| 2006/0129221 | A1 | 6/2006 | Heruth |

* cited by examiner

*Primary Examiner* — Scott Getzow
*Assistant Examiner* — Amanda Patton

(57) ABSTRACT

An apparatus for managing a lead of an implantable medical device includes a lead retention element and a fixation element. The lead retention element has a proximal end, a distal end, and a lumen extending from the proximal end to the distal end. The lumen is configured to slidably receive the lead. The fixation element is configured to fix the lead retention element relative to the implantable medical device in an orientation orthogonal to a lead receptacle of the device such that the proximal end of the lead retention element is closer to an opening of the lead receptacle than the distal end of the retention element. The distal end of the lead retention element is configured to firmly engage the lead to resist proximal sliding of the lead in the lumen of the retention element once the lead has been moved distally through the lumen.

9 Claims, 8 Drawing Sheets

IMPLANTABLE LEAD MANAGEMENT

CROSS-REFERENCE TO RELATED APPLICATIONS

The present application claims priority from U.S. Provisional Patent Application No. 61/161,906, filed Mar. 20, 2009, the entire disclosure of which is incorporated herein by reference.

FIELD

This application relates to implantable medical devices, more particularly devices employing medical leads and apparatuses for managing implanted leads.

BACKGROUND

Implantable medical devices are used to treat a variety of diseases, and their use is increasing. Many implantable medical devices employ medical leads to deliver electrical therapy to a patient or to monitor patient parameters. The leads are connected to the active device, which is typically implanted subcutaneously in the patient, and extend from the implanted device to a target location of the patient. The leads typically have a length greater than needed to extend from the device to the target location to ensure that the lead will be of sufficient length for almost all patients and almost all circumstances. Typically the lead is tunneled from the subcutaneous pocket to the target location. Excess lead length is then wrapped or coiled and placed in the subcutaneous pocket. The manner in which the lead is wrapped or coiled can vary from implanting surgeon to implanting surgeon and can affect, among other things, flex life performance of the lead, the extent of lead abrasion, and the size of the implant pocket and corresponding incision.

Problems with lead abrasion may be exacerbated with rechargeable active implantable medical devices and excess coiled lead. If the coiled excess lead or a portion of the lead crosses the face of the device between the device and the patient's skin, the likelihood of lead abrasion may increase. Because the primary recharge coil of an external recharge head is placed adjacent the patient's skin in a location over the implanted device, the lead may be impacted between the recharge head and the implanted device causing abrasion of the lead.

BRIEF SUMMARY

Apparatuses for managing excess lead length in proximity to an implanted medical device are described herein. The apparatuses may improve flex life performance, reduce lead abrasion, or may decrease the size of the implant pocket.

In various embodiments, an apparatus for managing a lead of an implantable medical device includes a lead retention element and a fixation element. The lead retention element has a proximal end, a distal end, and a lumen extending from the proximal end to the distal end. The lumen is configured to slidably receive the lead. The fixation element is configured to fix the lead retention element along a side surface of the implantable medical device in an orientation orthogonal to a lead receptacle of the device such that the proximal end of the lead retention element is closer to an opening of the lead receptacle than the distal end of the retention element. The distal end of the lead retention element is configured to snugly engage the lead to resist proximal sliding of the lead in the lumen of the retention element once the lead has been moved distally through the lumen.

Figure 1:
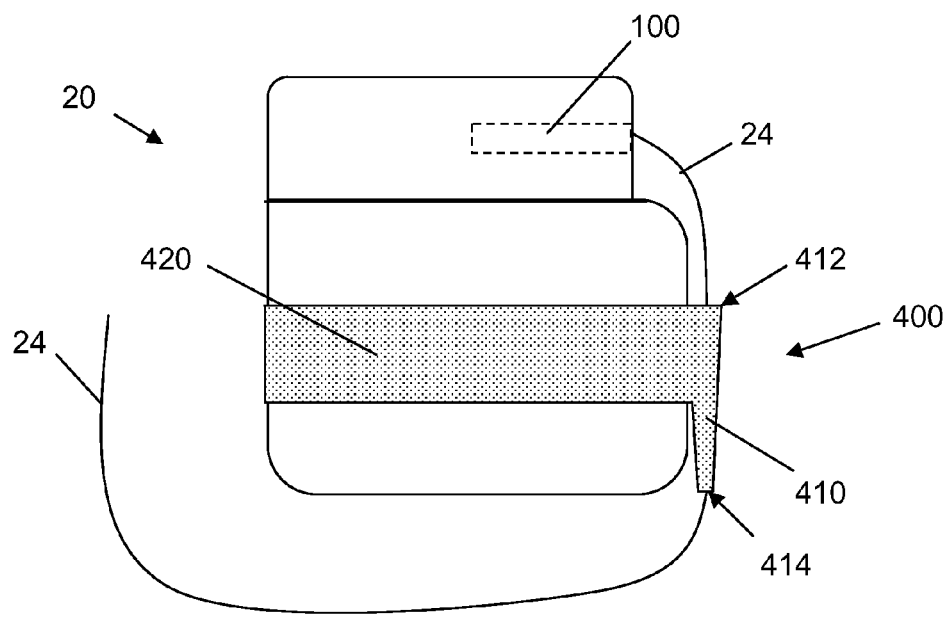
FIG. 1 is schematic side view of a device, lead, and a lead management apparatus.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

The present disclosure relates to apparatuses for managing excess lead length in proximity to an implanted medical device. The apparatuses may improve flex life performance, reduce lead abrasion, or may decrease the size of the implant pocket.

Referring now to FIGS. 1-10, exemplary embodiments of lead management apparatuses 400, or portions thereof, are shown. The lead management apparatuses 400 include a lead retention element 410 and a fixation element 420. The fixation element or portion 420 is configured to fix the lead retention element or portion 410 relative to the implantable medical device 20 in an orientation orthogonal to a lead receptacle 100 of the device 20 such that the proximal end 412 of the lead retention element 410 is closer to the opening of the lead receptacle 100 that the lead 24 exits than to the distal end 414 of the retention element 410. A lumen 430 extends through the retention element 410 from the proximal end 412 to the distal end 414. The lumen 430 of the retention element 410 is configured to slidably receive a lead 24. The distal end 414 of the retention element 410 is configured to firmly engage the lead 24 to resist proximal sliding of the lead 24 in the lumen 430 of the retention element 410 once the lead 24 has been moved (e.g. pushed or pulled) distally through the lumen 430.

Referring now to the embodiment in FIG. 2, in which a longitudinal cross section of a lead retention element 410 is shown, the distal end 414 of the retention element 410, in a relaxed state, has an inner diameter i.d. defined by the lumen 430 that is the same as or smaller than the outer diameter of the lead that it is configured to retain. Such an inner diameter i.d. allows the distal end 414 to firmly engage the lead. In many embodiments, the inner diameter i.d. of the distal end 414 is smaller than the outer diameter of the lead. In such embodiments, the distal end 414 of the retention element is formed from a material capable of resilient distension to allow the lead to pass through the distal end of the element via the lumen. Resiliency of the material and biasing towards the relaxed smaller inner diameter i.d. state facilitates snug engagement of the lead. To achieve such properties, the retention element or the entire lead maintenance apparatus may be made of an elastomeric polymer, such as silicone.

Figure 2A:
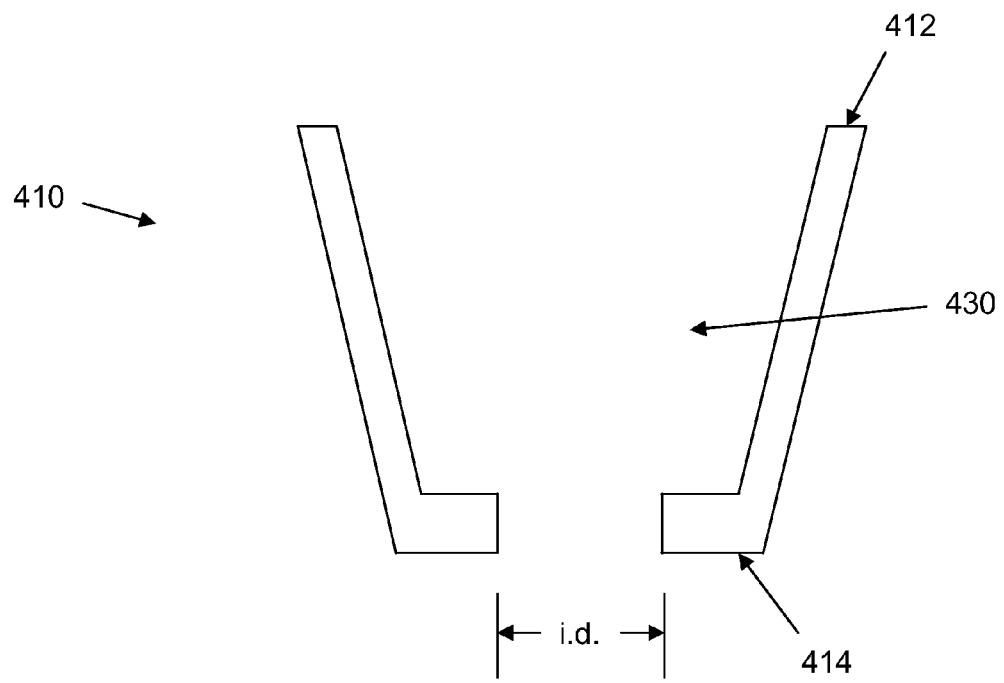
FIG. 2A is a schematic of a longitudinal cross section of a lead retention feature of an exemplary embodiment of a lead management apparatus as shown in FIG. 1.
Figure 2B:
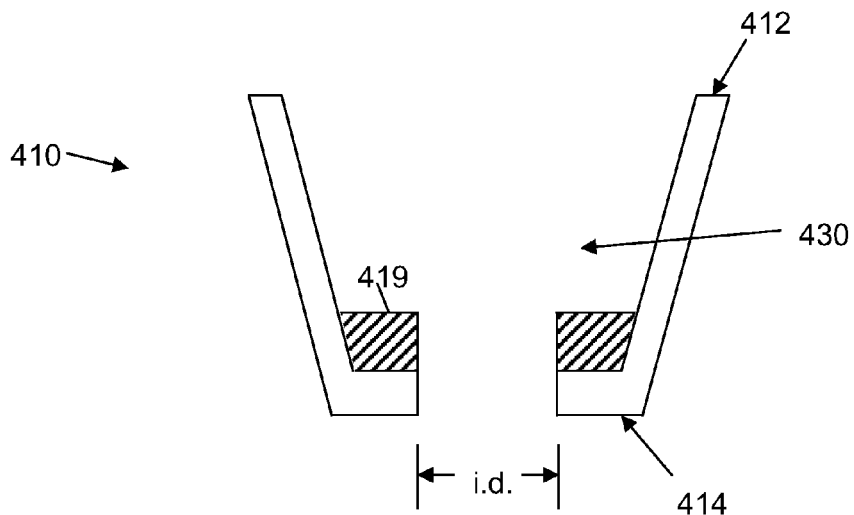
FIG. 2B is a schematic of a longitudinal cross section of a lead retention feature of an exemplary embodiment of a lead management apparatus as shown in FIG. 1.
Figure 2C:
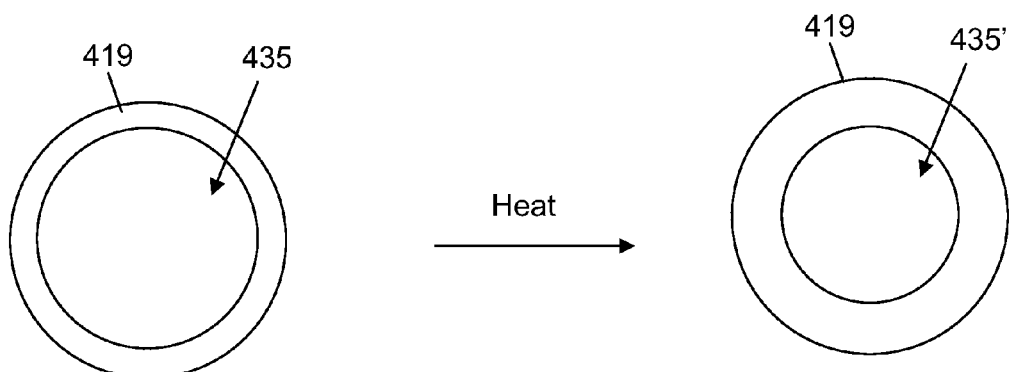
FIG. 2C is a top-down view of an exemplary embodiment of a constriction feature as shown in FIG. 2B.
Figure 2D:
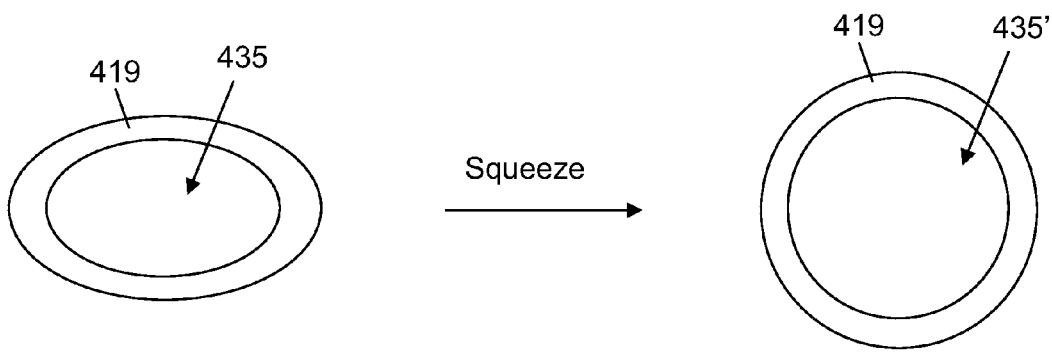
FIG. 2D is a top-down view of an exemplary embodiment of a constriction feature as shown in FIG. 2B.

In the embodiment depicted in FIG. 2A, the lumen 430 is tapered such that the inner diameter decreases along the length of the retention element from the proximal end 412 towards the distal end 414. Such an arrangement allows for easy insertion and pulling through of the lead. If the lead were snugly engaged along the entire length of the retention element, a great deal of force may be required to push or pull the lead through the lumen 430 of the retention element. As shown in FIG. 2B, the lead retention element 410 may include a constriction feature 419 configured to grippingly engage and retain a lead. The constriction feature 419 may take any suitable form. For example and with reference to FIG. 2C, the constriction feature may have a first inner diameter 435 through which the lead may be slid and a second inner diameter 435' smaller than the first inner diameter 435. In the second inner diameter state, the constriction feature 419 is configured to grippingly engage and retain a lead. In an embodiment, the constriction feature 419 may change from the first state having the first inner diameter 435 to the second state having the second inner diameter 435' when heated from room temperature to body temperature. By way of example, the constriction feature 419 may be a shape memory coil that is constricted in the first state and relaxes to the second state upon heating to body temperature following implantation. Any suitable shape memory material, such as nitinol, may be used. As shown in the embodiment depicted in FIG. 2C, constriction feature 419 may be formed of a resilient material having an oblong cross-sectional shape in its relaxed configuration. The oblong lumen 435 in the relaxed state is configured to grippingly engage the lead and to prevent or restrict sliding of the lead through the lumen 435. A squeezing force may be applied to the constriction feature 419 to cause lumen 435' to assume a more cylindrical cross-sectional shape and allow the lead to be slid through the lumen 435'. Upon release of the squeezing force, the constriction feature 419 may grippingly engage the lead. Of course, any other suitable constriction feature may be employed.

Figure 3:
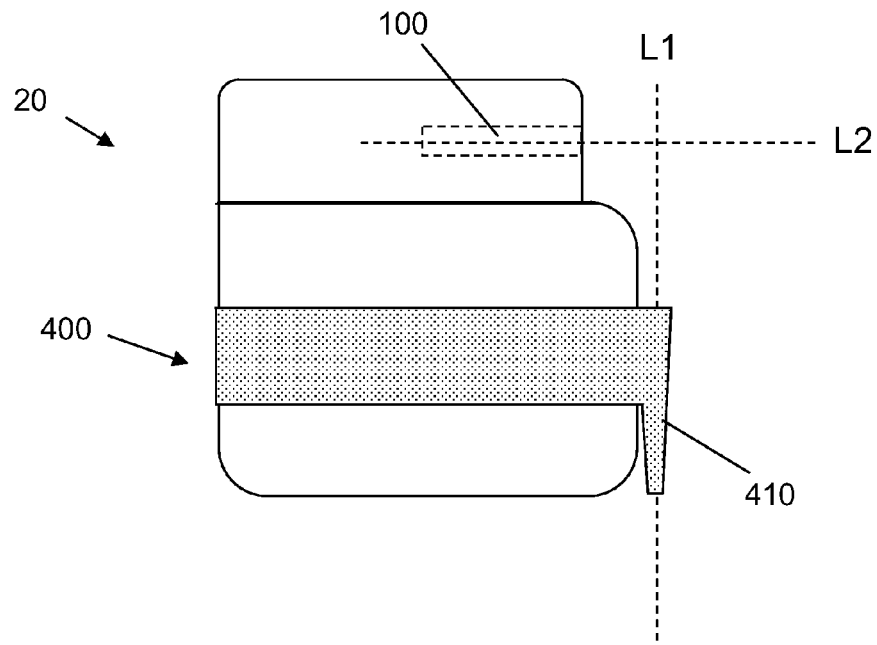
FIG. 3 is a schematic side view of a device and a lead management apparatus.

Referring now to FIG. 3, a schematic side view of a device 20 and associated lead retention apparatus 400 is shown. The device 20 and apparatus 400 depicted in FIG. 3 is the same as the device and apparatus shown in FIG. 1. Line L1 is an axially centered line extending through the lumen of the lead retention element 410 of apparatus 400. Line L2 is an axially centered line extending through the lead receptacle 100 of the device 20. As shown, the lead retention element 410 is oriented orthogonally relative to the lead receptacle 100. As used herein, "orthogonal", as it related to the orientation of a lead retention element relative to a lead receptacle of an implantable medical device, means that an axially centered line extending through the lead-retaining lumen of the retention element intersects or lies generally at a right angle (e.g., between about 70 and 110 degrees, between about 80 and 100 degrees, between about 85 and 95 degrees, or about 90 degrees) to an axially centered line extending through the lead receptacle. It will be understood that if the cross-sectional shape of the lumen of the lead retention element or of the lead receptacle is other than circular, the axial center of such a structure is the geometric center for the purposes of this disclosure.

Figure 4A:
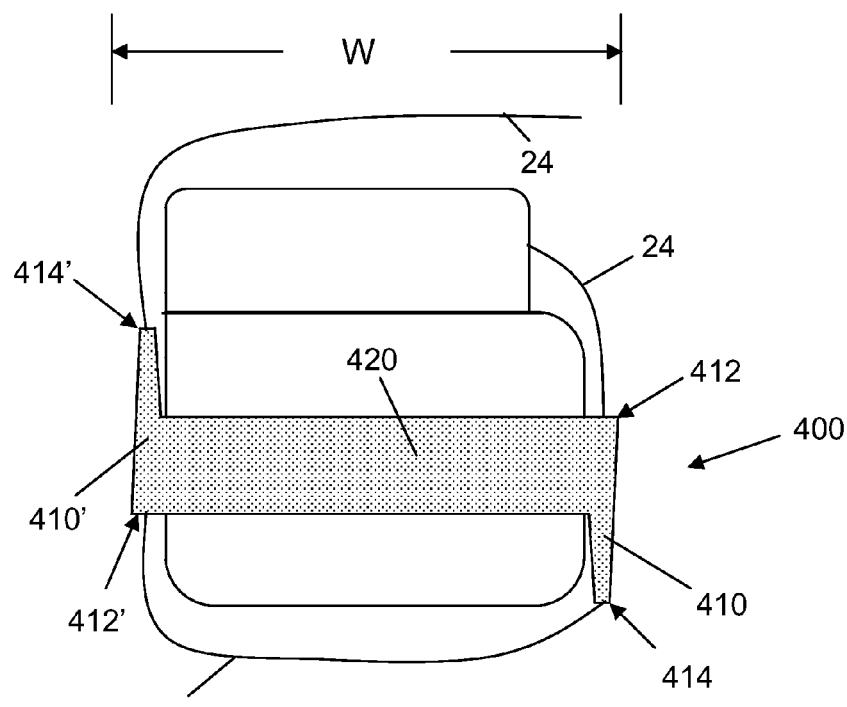
FIG. 4A is a schematic side view of a device, lead, and a lead management apparatus.

Referring now to FIG. 4A, a lead management apparatus 400 may contain an additional retention element 410'. The additional retention element 410' may be substantially the same as the first retention element 410. That is, the additional retention element 410' has a proximal end 412', a distal end 410', and a lumen extending from the proximal end 412' to the distal end 410'. The lumen is configured to slidably receive the lead 24. The distal end 414' is configured to firmly engage the lead 24 to resist proximal sliding of the lead 24 in the lumen of the additional retention element 410' once the lead 24 has been moved distally through the lumen. The fixation element 420 is configured to fix the additional lead retention element 410' along a side surface of the implantable medical device generally opposing the side surface along which the first retention element 410 is fixed. As shown in FIG. 12, a device combined with the depicted lead management apparatus 400 may have an effective width W smaller than a device without an associated lead management apparatus (compare; e.g., FIG. 4A to FIG. 4B). By keeping the lead 24 in close proximity to the device, the effective width W is minimized, allowing for a smaller surgical pocket and incision. Smaller surgical pockets and incisions are likely to reduce complications, such as infection, and patient discomfort. In addition, attempting to force a device having a large effective width W into a small surgical pocket may result in lead kinking and reliability issues that may be mitigated through the lead management embodiments discussed and contemplated herein.

Figure 5:
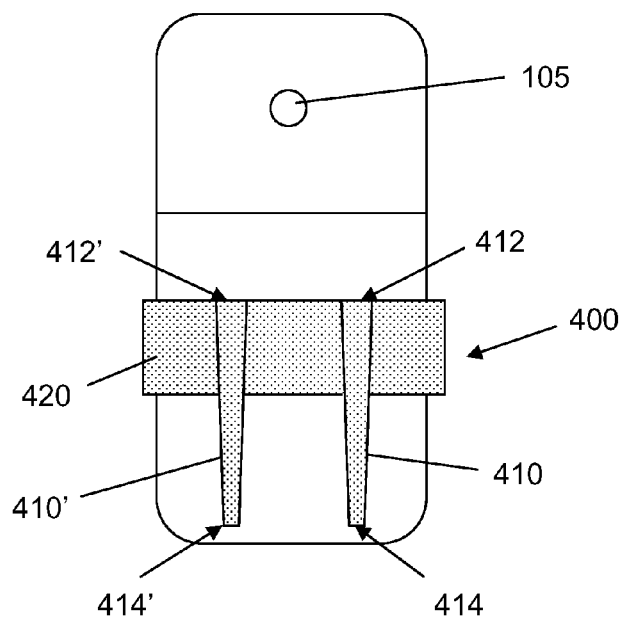
FIG. 5 is a schematic front view of an embodiment of the device and lead management apparatus as shown in FIG. 1 or FIG. 3.
Figure 6:
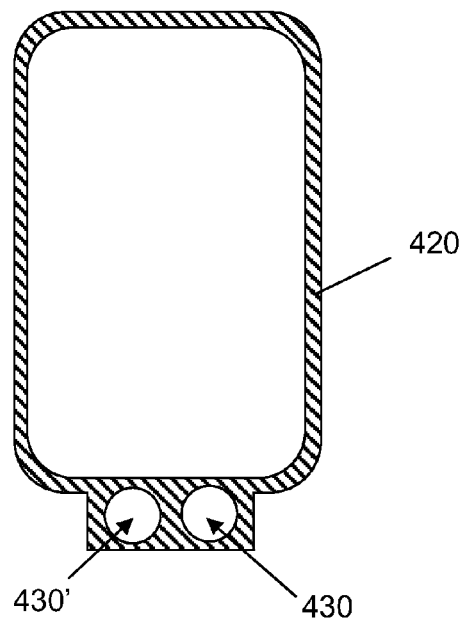
FIG. 6 is a schematic top-down view of a lead management apparatus as depicted in FIG. 11.
Figure 7:
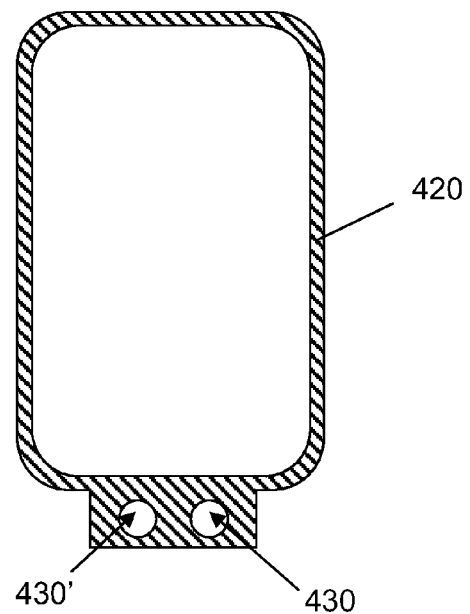
FIG. 7 is a schematic bottom-up view of a lead management apparatus as depicted in FIG. 11.

Referring now to FIGS. 5-7, a lead management apparatus 400 may contain an additional retention element 410', where the fixation element 420 is configured to fix the additional lead retention element 410' in a side-by-side relationship with the first retention element 410. Such a configuration allows the lead to be wrapped multiple times around the device. As shown in the top-down view in FIG. 14, the lumens 430, 430' of the first and second retention elements form a larger inner diameter at the proximal end than at the distal end 414, 414' (see FIG. 15).

In the embodiment depicted in FIGS. 1-7, the fixation element 420 forms a band configured to be disposed about an implantable medical device. The fixation element 420 may be formed from elastomeric material that is resilient. Accordingly, the band formed by the fixation element 420 may have an inner circumferential dimension, in a relaxed state, that is smaller than an outer circumferential dimension of the implantable medical device. The band formed by the fixation element 420 may then be resiliently expandable to form a sufficiently large inner circumferential dimension to be disposed about the implantable medical device. Biasing of the band to its relaxed circumferential dimension may then cause the fixation element 420 to anchor the lead management apparatus to the device.

Figure 8A:
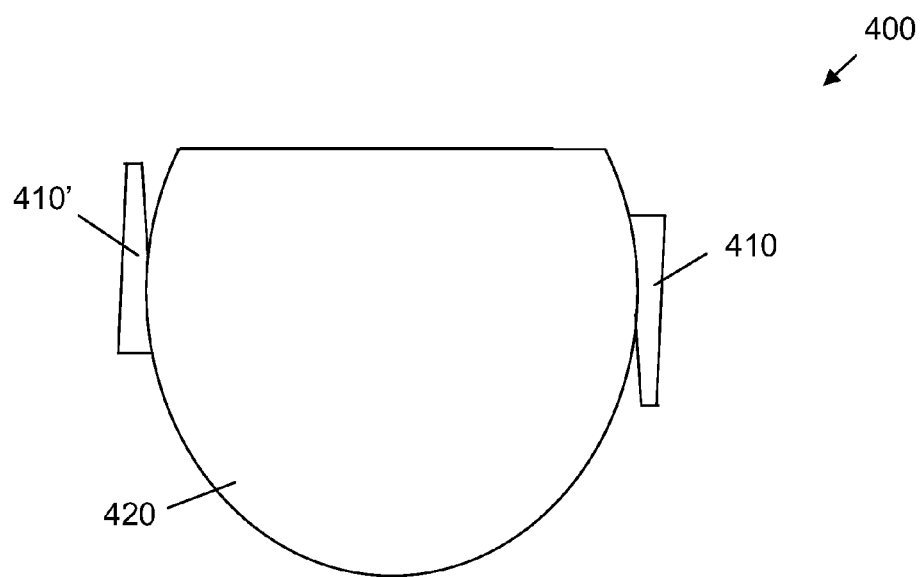
FIG. 8A is a schematic side view of a lead management apparatus.
Figure 8B:
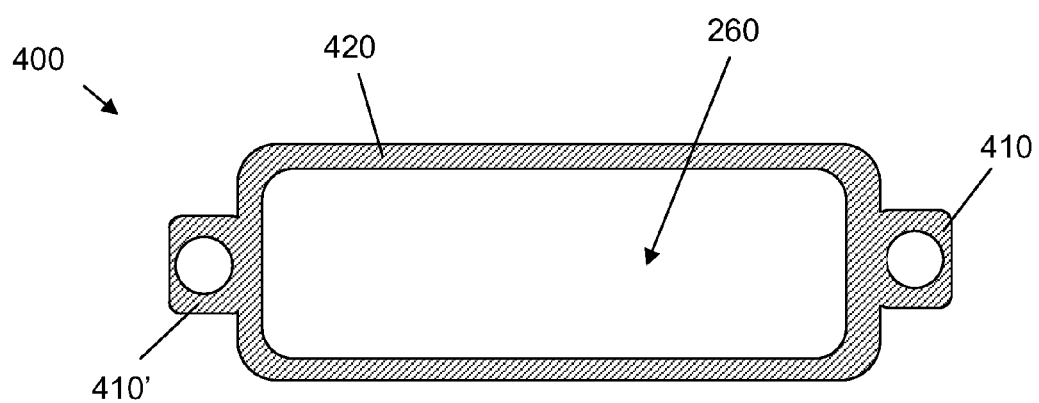
FIG. 8B is a top-down view of an exemplary embodiment of an apparatus shown in FIG. 8A.
Figure 8C:
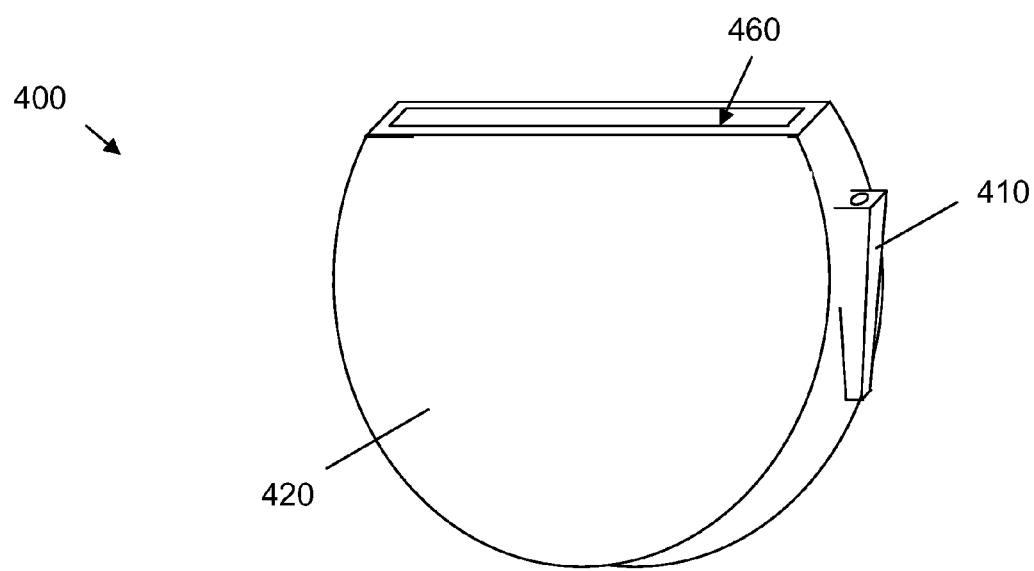
FIG. 8C is a schematic perspective view of an exemplary embodiment of the apparatus shown in FIG. 8A.
Figure 9:
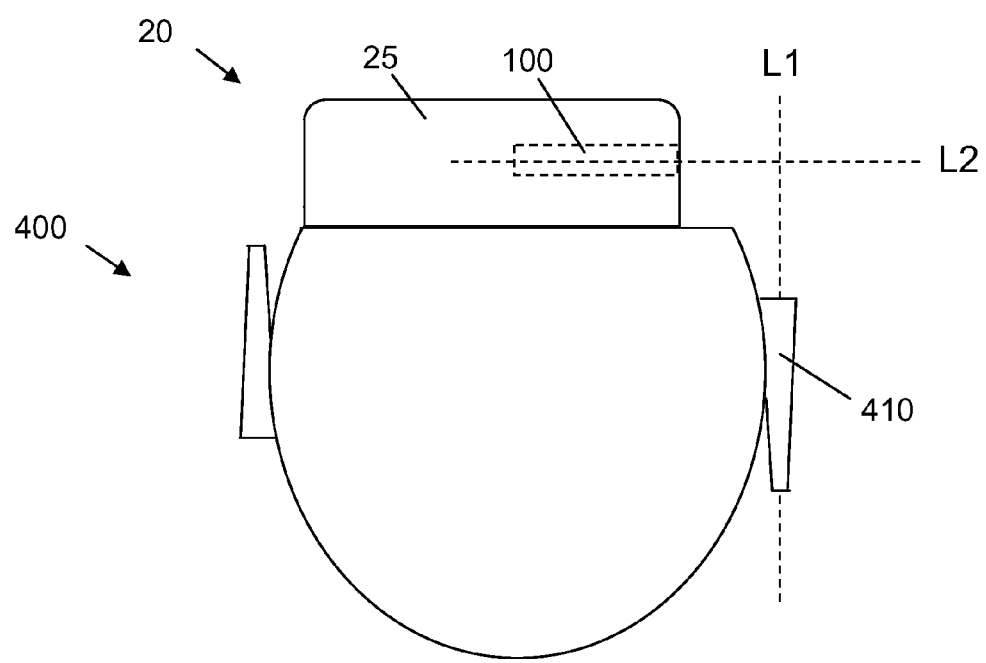
FIG. 9 is a schematic side view of a lead management apparatus placed about an implantable medical device.
Figure 10:
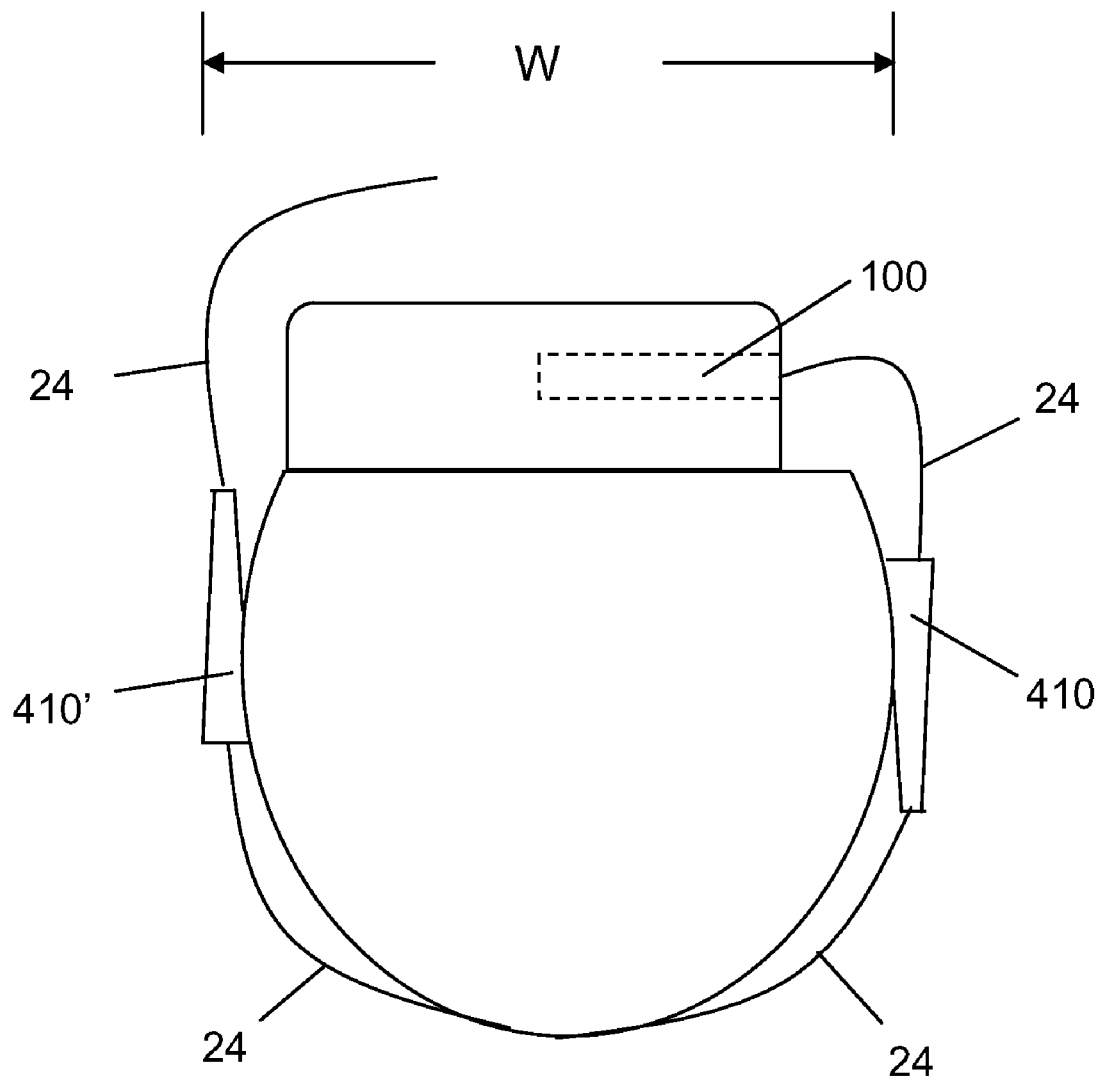
FIG. 10 is a schematic side view of a lead management apparatus placed about an implantable medical device, with an associated lead.

Referring now to FIGS. 8-10, alternative embodiments of a lead retention apparatus are shown. FIGS. 8A-C show schematic side, top, and perspective views of an apparatus 400 configured to be placed about an implantable medical device. The apparatus 400 includes a fixation element 410 in the form of a boot configured to receive the device and includes retention elements 410, 410'. The boot fixation element 420 forms a cavity in communication with an opening 460, into which an implantable medical device may be placed.

Figure 4B:
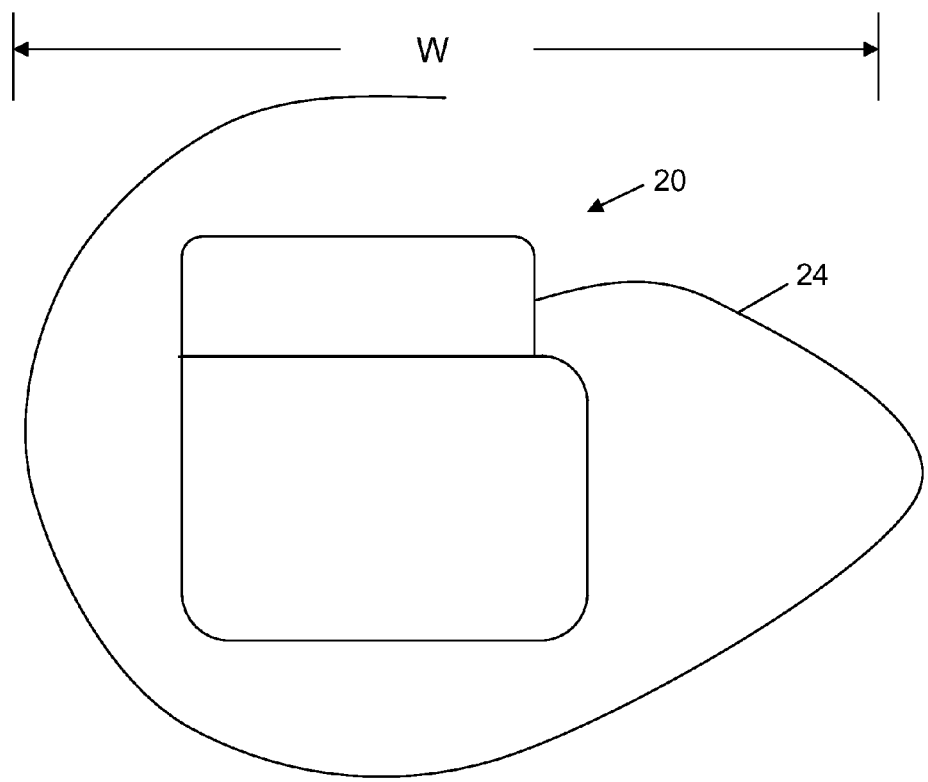
FIG. 4B is a schematic side view of the device and lead depicted in FIG. 4A, without the lead management apparatus.

FIG. 9 is a schematic side view of a lead retention apparatus 400 and an implantable medical device 20. The depicted lead retention apparatus 400 is the same as the apparatus depicted in FIGS. 8A-C. The device 20, e.g. a device depicted in FIG. 4B, is inserted into the cavity of the boot fixation element 420. The boot is configured to firmly engage the device 20. In the depicted embodiment, a connection header portion 25 of the device 20 extends out of the boot, to allow a lead to be operably coupled to lead receptacle 100. Line L1 is an axially centered line extending through the lumen of the lead retention element 410 of apparatus 400. Line L2 is an axially centered line extending through the lead receptacle 100 of the device 20. As shown, the lead retention element 410 is oriented orthogonally relative to the lead receptacle 100.

As shown in FIG. 10, the retention elements 410, 410' retain the lead 24 exiting the receptacle 100 of the device to provide excess lead maintenance, reducing the overall effective width W of the device (compared to the effective width W of a device 20 without a corresponding lead maintenance apparatus shown in FIG. 4B). By keeping the lead 24 in close proximity to the device, the effective width W is minimized, allowing for a smaller surgical pocket and incision. Smaller surgical pockets and incisions are likely to reduce complications, such as infection, and patient discomfort.

The lead management apparatuses as described herein, or portions thereof, may be made of any suitable, medically acceptable material. Examples of polymeric materials that may be employed include organic polymers such as silicones, polyamines, polystyrene, polyurethane, acrylates, polysilanes, polysulfone, methoxysilanes, and the like. Other polymers that may be utilized include polyolefins, polyisobutylene and ethylene-alphaolefin copolymers; acrylic polymers and copolymers, ethylene-covinylacetate, polybutylmethacrylate; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; polycarbonates; polyoxymethylenes; polyimides; polyethers; epoxy resins; polyurethanes; rayon; rayon-triacetate; cellulose; cellulose acetate, cellulose butyrate; cellulose acetate butyrate; cellophane; cellulose nitrate; cellulose propionate; cellulose ethers; carboxymethyl cellulose; polyphenyleneoxide; and polytetrafluoroethylene (PTFE). In many embodiments, an apparatus as described herein is formed from an elastomeric polymer, such as silicone.

The apparatus may be molded or otherwise formed. In some embodiments, the apparatus may be formed such that the portion of the apparatus grippingly engages the device. In some embodiments, adhesive, such as medical adhesive, may be employed to bond the apparatus, or portions thereof, to the device.

In various embodiments, a therapeutic agent is incorporated into or onto at least a portion of an apparatus as described herein. Any suitable therapeutic agent may be included in the apparatus. Examples of suitable therapeutic agents are described in U.S. Pre-Grant Published Patent Application Publication No. 2006/0129221, entitled "Tunneling Guide," published on Jun. 15, 2006, which published patent application is hereby incorporated herein by reference in its entirety to the extent that it does not conflict with the disclosure presented herein. By way of example, one or more anti-inflammatory agents, local anesthetics, analgesic, or anti-infective agents may be incorporated in or on an apparatus.

In some embodiments, an anti-infective agent is incorporated in or on at least a portion of an apparatus described herein. Preferably, the anti-infective agent is present in or on the apparatus, or may be eluted from the apparatus, in an amount sufficient to prevent an infection from forming in a pocket into which the device is implanted. It is also desirable that the anti-infective agent, in the concentration present in the apparatus or portion thereof, be nontoxic when implanted in the patient. It will be understood that more than one anti-infective agent may be present in or on the apparatus. Nonlimiting examples of such agents include antibiotics and antiseptics.

Any antibiotic suitable for use in a human may be used in accordance with various embodiments of the disclosure. An antibiotic may have bateriostatic or bacteriocidal activities. Nonlimiting examples of classes of antibiotics that may be used include tetracyclines (e.g. minocycline), rifamycins (e.g. rifampin), macrolides (e.g. erythromycin), penicillins (e.g. nafcillin), cephalosporins (e.g. cefazolin), other beta-lactam antibiotics (e.g. imipenem, aztreonam), aminoglycosides (e.g. gentamicin), chloramphenicol, sufonamides (e.g. sulfamethoxazole), glycopeptides (e.g. vancomycin), quinolones (e.g. ciprofloxacin), fusidic acid, trimethoprim, metronidazole, clindamycin, mupirocin, polyenes (e.g. amphotericin B), azoles (e.g. fluconazole) and beta-lactam inhibitors (e.g. sulbactam). Nonlimiting examples of specific antibiotics that may be used include minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, and nystatin. One of ordinary skill in the art will recognize other antibiotics that may be used.

It is desirable that the selected antibiotic(s) kill or inhibit the growth of one or more bacteria that are associated with infection following surgical implantation of a medical device. Such bacteria are recognized by those of ordinary skill in the art and include *Stapholcoccus aureus* and *Staphlococcus epidermis*. Preferably, the antibiotic(s) selected are effective against strains of bacteria that are resistant to one or more antibiotic.

To enhance the likelihood that bacteria will be killed or inhibited, it may be desirable to combine one or more antibiotics. It may also be desirable to combine one or more antibiotics with one or more antiseptics. It will be recognized by one of ordinary skill in the art that antimicrobial agents having different mechanisms of action or different spectrums of action may be most effective in achieving such an effect. In one exemplary embodiment, a combination of rifampin and minocycline is used.

Any antiseptic suitable for use in a human may be used in accordance with various embodiments of the disclosure. Antiseptics are agents capable of killing or inhibiting the growth of one or more of bacteria, fungi, or viruses. Antiseptics include disinfectants. Some examples of antiseptics include hexachlorophene, cationic bisiguanides (i.e. chlorhexidine, cyclohexidine) iodine and iodophores (i.e. povidone-iodine), para-chloro-meta-xylenol, triclosan, furan medical preparations (i.e. nitrofurantoin, nitrofurazone), methenamine, aldehydes (glutaraldehyde, formaldehyde), silver sulfadiazine and alcohols. One of ordinary skill in the art will recognize other antiseptics.

It is desirable that the selected antiseptic(s) kill or inhibit the growth of one or more microbes that are associated with infection following surgical implantation of a medical device. Such bacteria are recognized by those of ordinary skill in the art and include *Stapholcoccus aureus, Staphlococcus epidermis, Pseudomonus auruginosa,* and *Candidia*.

To enhance the likelihood that microbes will be killed or inhibited, it may be desirable to combine one or more antiseptics. It may also be desirable to combine one or more antiseptics with one or more antibiotics. It will be recognized by one of ordinary skill in the art that antimicrobial agents having different mechanisms of action or different spectrums of action may be most effective in achieving such an effect. In a particular embodiment, a combination of chlorohexidine and silver sulfadiazine is used.

An anti-infective agent, such as an antibiotic or antiseptic, may be present in the apparatus at any concentration effective, either alone or in combination with another anti-infective agent, to prevent an infection within a pocket into which the apparatus is implanted. Generally, an antiseptic agent may be present in the apparatus at a range of between about 0.5% and about 20% by weight. For example, the anti-infective agent may be present in the apparatus or portion thereof at a range of between about 0.5% and about 15% by weight or between about 0.5% and about 10% by weight.

An anti-infective agent may be incorporated into or on a polymeric apparatus using any known or developed technique. For example, the anti-infective agent may be adhered to a surface of the apparatus, adsorbed into the apparatus, or compounded into the polymeric material that forms the apparatus. Accordingly, the anti-infective material may be embedded, coated, mixed or dispersed on or in the material of the apparatus. In various embodiments, the anti-infective agent may be incorporated into the polymeric apparatus as taught in U.S. Pat. Nos. 5,217,493 or 5,624,704.

Thus, exemplary embodiments of implantable lead management are disclosed. One skilled in the art will appreciate that the present disclosure can be practiced with embodiments other than those disclosed. The disclosed embodiments are presented for purposes of illustration and not limitation, and the present disclosure is limited only by the claims that follow.

What is claimed is:

1. An apparatus for managing a lead operably coupled to an implantable medical device, comprising:
   a lead retention element having a proximal end and a distal end and defining a lumen extending from the proximal end to the distal end, the lumen configured to slidably receive the lead; and
   a fixation element configured to fix the lead retention element relative to the implantable medical device in an orientation orthogonal to a lead receptacle of the device such that the proximal end of the lead retention element is closer to an opening of the lead receptacle than the distal end of the retention element,
   wherein the entire an aparatus is made of an elastomeric polymer;
   wherein the distal end of the lead retention element is configured to resiliently distend to allow the lead to be pass through the lumen of the retention element and further to firmly engage the lead to resist proximal sliding of the lead in the lumen of the retention element once the lead has been moved distally through the lumen;
   wherein the distal end of the retention element is configured such that an inner diameter defined by the lumen is biased to be smaller than the outer diameter of the lead when the retention element is in a relaxed state before the lead is moved into the lumen, and the resiliency of the distal end of the retention element and biasing towards the inner diameter being smaller than the outer diameter of the lead facilitates engagement between the distal end of the retention element and the lead; and
   wherein the fixation element comprises a band, the band having an inner circumferential dimension that is biased to be smaller, when the fixation is in a relaxed state and not on the implantable medical device an outer circumferential dimension of the implantable medical device, and the band is resiliently expandable such that the inner circumferential dimension of the band can expand to be sufficiently large to be disposed around the implantable medical device where the biasing of the inner circumferential dimension to be smaller than the outer circumferential dimension of the implantable medical device anchors the apparatus to the implantable medical device.

2. The apparatus according to claim 1, wherein the proximal end of the retention element has an inner diameter formed by the lumen, and wherein the inner diameter of the proximal end is greater than the outer diameter of the lead.

3. The apparatus according to claim 1, wherein the inner diameter of the retention element defined by the lumen is tapered such that the inner diameter decreases along the length of the retention element from the proximal end towards the distal end.

4. The apparatus according to claim 1, further comprising an additional retention element having a proximal end and a distal end and a lumen extending from the proximal end to the distal end, the lumen configured to slidably receive the lead,
   wherein the fixation element is configured to fix the additional lead retention element relative to the implantable medical device generally opposing the side surface along which the first retention element is fixed, wherein the distal end of the additional lead retention element is configured to firmly engage the lead to resist proximal sliding of the lead in the lumen of the additional retention element once the lead has been moved distally through the lumen.

5. The apparatus according to claim 1, further comprising an additional retention element having a proximal end and a distal end and a lumen extending from the proximal end to the distal end, the lumen configured to slidably receive the lead, wherein the fixation element is configured to fix the additional lead retention element in a side-by-side relationship with the first retention element, wherein the distal end of the additional lead retention element is configured to firmly engage the lead to resist proximal sliding of the lead in the lumen of the additional retention element once the lead has been moved distally through the lumen.

6. The apparatus according to claim 1, wherein the apparatus comprises one or more elutable therapeutic agents.

7. The apparatus according to claim 1, wherein the one or more elutable therapeutic agents comprise an anti-infective agent.

8. The apparatus according to claim 1, wherein the one or more elutable therapeutic agents comprise minocycline and rifampin.

9. A system comprising:
the apparatus according claim 8; and
the implantable medical device.

* * * * *

UNITED STATES PATENT AND TRADEMARK OFFICE
CERTIFICATE OF CORRECTION

| | |
|---|---|
| PATENT NO. | : 8,209,016 B2 |
| APPLICATION NO. | : 12/725548 |
| DATED | : June 26, 2012 |
| INVENTOR(S) | : Steve T. Deininger |

It is certified that error appears in the above-identified patent and that said Letters Patent is hereby corrected as shown below:

In the Claims

Column 8, line 24: "wherein the entire an aparatus is made" should read -- wherein the entire apparatus is made --.

Column 8, line 44: "implantable medical device an outer" should read -- implantable medical device, an outer --.

Signed and Sealed this
Third Day of March, 2015

Michelle K. Lee
*Deputy Director of the United States Patent and Trademark Office*